United States Patent [19]

Kiyoura

[11] 4,242,525

[45] Dec. 30, 1980

[54] PROCESS FOR PRODUCING SALTS OF PYRUVIC ACID

[75] Inventor: Tadamitsu Kiyoura, Kamakura, Japan

[73] Assignee: Mitsui Toatsu Chemicals, Incorporated, Tokyo, Japan

[21] Appl. No.: 28,695

[22] Filed: Apr. 10, 1979

[30] Foreign Application Priority Data

Apr. 17, 1978 [JP] Japan .................................. 53-44267
Aug. 31, 1978 [JP] Japan ................................ 53-105619
Jan. 19, 1979 [JP] Japan .................................... 54-3992

[51] Int. Cl.$^3$ .............................................. C07C 59/19
[52] U.S. Cl. ..................................................... 562/577
[58] Field of Search .......................................... 562/577

[56] References Cited

U.S. PATENT DOCUMENTS 4,136,111  1/1979  Feldman .............................. 562/577

FOREIGN PATENT DOCUMENTS 523190  5/1931  Fed. Rep. of Germany ........... 562/577
176288 12/1965  U.S.S.R. ................................... 562/577

*Primary Examiner*—Natalie Trousof
*Assistant Examiner*—G. T. Breitenstein

[57] ABSTRACT

A salt of pyruvic acid is formed by oxidizing a salt of lactic acid with an oxygen-containing gas in a water-containing solvent in the presence of a catalyst. The catalyst used herein comprises (a) at least one component selected from platinum and palladium and (b) at least one component selected from lead, tin, tellurium, indium, bismuth, and compounds of these elements. The resulting pyruvate is isolated in the form of a solid by concentrating the catalyst-free reaction mixture and then mixing isopropyl alcohol therewith.

22 Claims, No Drawings

PROCESS FOR PRODUCING SALTS OF PYRUVIC ACID

BACKGROUND OF THE INVENTION (1) Field of the Invention

This invention relates to a novel process for producing salts of pyruvic acid by the oxidation of salts of lactic acid with an oxygen-containing gas.

(2) Description of the Prior Art

Pyruvic acid and salts thereof are important intermediates found in the pathway of carbohydrate metabolism within the living body. Industrially, these compounds are useful as the starting materials for the production of L-tryptophan by a fermentation process in which indole, pyruvate, and ammonia are reacted by the action of tryptophanase. In addition, they have great utility in the production of L-cysteine by a fermentation process using pyruvate, ammonia, and hydrogen sulfide as starting materials and in the production of L-DOPA by a fermentation process using catechol, pyruvate, and ammonia as starting materials.

In the prior art, a number of processes for producing pyruvic acid and salts thereof have been proposed. They include, for example, (1) a process in which sodium cyanide and acetyl chloride are reacted to form acetyl cyanide and the cyanide is then hydrolyzed; (2) a process in which tartaric acid is dry-distilled in the presence of potassium hydrogensulfate; (3) a fermentation process using lactic acid as starting material; (4) a process in which lactic esters are oxidized, for example, with potassium permanganate; (5) a process in which propylene glycol is oxidized; and the like.

However, the above-described processes have various drawbacks. Specifically, the process (1) is disadvantageous in that the starting materials are expensive, the yield of the desired product is low, and the formation of considerable amounts of by-products makes it difficult to separate and purify the desired product. In the process (2), the starting material (tartaric acid) is expensive, the subsidiary material (potassium hydrogensulfate) is consumed in large amounts, and the yield is not so high as would be desirable. In the process (3), α-ketoglutaric acid is inevitably formed as a by-product. The process (4), in which lactic esters are oxidized with a suitable agent such as potassium permanganate, has the disadvantages that the potassium permanganate is consumed in an amount greater than its chemical equivalent and that the recovery and re-oxidation of manganese require extremely complicated procedures. The process (5) based on the oxidation of propylene glycol is not suitable for the selective production of pyruvates because by-products such as lactates are formed in considerable amounts.

SUMMARY OF THE INVENTION

Accordingly, it is an object of the present invention to provide a novel improved process for producing salts of pyruvic acid which overcomes the drawbacks of the prior art.

It is another object of the present invention to provide a process for producing salts of pyruvic acid by the oxidation of salts of lactic acid in a water-containing solvent in the presence of a novel catalyst.

It is a further object of the present invention to provide a novel method of isolating the resulting pyruvate from the reaction mixture.

These objects of the present invention are accomplished by providing a process for producing a salt of pyruvic acid which comprises oxidizing a salt of lactic acid with an oxygen-containing gas in a water-containing solvent in the presence of a catalyst comprising (a) at least one component selected from the group consisting of platinum and palladium and (b) at least one component selected from the group consisting of lead, tin, tellurium, indium, bismuth, and compounds of these elements.

The resulting pyruvate is isolated in the form of a solid by concentrating the reaction mixture, if necessary, and then mixing isopropyl alcohol therewith.

DETAILED DESCRIPTION OF THE INVENTION

The catalysts which can be used in the process of the invention are those comprising (a) at least one component (hereinafter referred to as "platinum metal component") selected from the group consisting of platinum and palladium and (b) at least one component (hereinafter referred to as "additional component") selected from the group consisting of lead, tin, tellurium, indium, bismuth, and compounds of these elements.

Among the catalysts comprising a combination of a noble metal and a base metal, the Lindlar catalyst is well known. In this catalyst, palladium is poisoned by lead acetate so that acetylenic triple bonds may be hydrogenated to ethylenic double bonds but the latter may not be hydrogenated to single bonds. Thus, the poisoning effect of the lead compound is utilized to reduce the catalytic activity of the noble metal and thereby improve the selectivity to the desired reaction product.

In the catalyst of the invention, platinum and/or palladium are combined with, for example, a lead compound as an additional component. In contrast to the Lindlar catalyst, however, the lead compound serves to enhance the catalytic activity of the platinum metals and thereby increase greatly the rate of oxygen absorption due to the oxidation reaction involved. That is, in the catalyst of the invention, such a base metal is used in order not to improve the selectivity to the desired reaction product owing to its poisoning effect on the platinum metals, but to enhance the catalyst activity of the platinum metals. As a result, the catalyst of the invention makes it possible to produce pyruvates from lactates in such a good yield as has been unattainable in the prior art.

It is essential to the production of pyruvates in good yield that the catalyst used in the process of the invention contains the above-defined additional component, together with platinum and/or palladium. If a conventional catalyst comprising platinum and/or palladium alone or platinum and/or palladium supported on a carrier is used, the yield of the desired pyruvate is extremely low or substantially zero.

Although these catalyst components may be used without any carrier, it is usually advantageous from an industrial point of view to support them on a carrier. The carriers useful for this purpose include, for example, activated carbon, alumina, diatomaceous earth, pumice, magnesia, and the like. However, activated carbon and alumina are used in typical cases.

When at least one platinum metal component selected from platinum and palladium is supported on a carrier, the amount of the platinum metal component should be in the range of from 0.1 to 20% by weight, and preferably from 0.5 to 10% by weight, and most preferably from 1 to 5% by weight, based on the weight of the carrier. When at least one additional component selected from lead, tin, tellurium, indium, bismuth, and compounds of these elements is supported on the carrier, together with the aforesaid platinum metal component, the amount of the additional component should be in the range of from 0.1 to 20% by weight, and preferably from 0.5 to 10% by weight, and most preferably from 1 to 5% by weight, based on the weight of the carrier.

The platinum metal component is usually used in elemental form, though they may be used in the form of compounds such as oxides. The additional component may be used either in elemental form or in the form of compounds. The compounds useful for this purpose include, for example, oxides, hydroxides, nitrates, sulfates, halides, carbonates, organic acid salts, and the like.

The catalysts which are useful in the process of the invention can be prepared by any conventional procedure. For example, a useful catalyst is obtained by mixing an aqueous solution of chloroplatinic acid and an aqueous solution of lead nitrate in a predetermined proportion, impregnating a carrier with this mixture, and reducing the impregnated carrier by a suitable agent such as formalin.

Commercially available noble metal catalysts can also be used in the process of the invention, if at least one additional component is applied thereto by suitable techniques such as impregnation. For example, a useful catalyst is prepared by providing a commercially available catalyst comprising palladium supported on activated carbon powder and impregnating it with an aqueous solution of lead acetate or lead nitrate. Alternatively, a commercially available catalyst comprising platinum supported on activated carbon powder may be used in such a manner that, prior to the oxidation reaction, this catalyst is incorporated into the reaction mixture and at least one additional component is added thereto in the form of a water-soluble compound.

The amount of catalyst used is not critical. However, in the case of a suspensoid system, a catalyst comprising the abovedefined components supported on a carrier is usually used in an amount of from 5 to 100 g per liter of the reaction mixture. The catalyst may be filtered off after each reaction cycle and used repeatedly over a long period of time.

The salts of lactic acid which can be used as starting materials in the process of the invention are being industrially mass-produced from acetaldehyde and cyanic acid and supplied at low prices. They include, for example, alkaline metal salts of lactic acid such as sodium lactate and potassium lactate; alkaline earth metal salts of lactic acid such as calcium lactate, ammonium lactate; and the like. However, sodium lactate is used in typical cases.

The water-containing solvents which can be used in the process of the invention include water and mixtures of water and other solvents that may be solvents miscible with water, such as dimethylformamide, diethylene glycol ethers, dioxane, and tertbutyl alcohol. Among these solvents, water is particularly preferred.

The concentration of the salt of lactic acid in the water-containing solvent should be in the range of from 2 to 30% by weight and preferably from 5 to 20% by weight. If the concentration is below the aforesaid lower limit, a great deal of expense will be required for the purpose of concentrating the reaction mixture and the amount of energy consumed in the agitation of the reaction mixture and in the supply of air will be increased excessively. If the concentration is above the aforesaid upper limit, the reaction rate will be reduced and side reactions will be promoted, thus leading to undesirable results.

The oxygen-containing gases which can be used in the process of the invention include oxygen gas, air, oxygen gas diluted with air or an inert gas such as nitrogen gas, and air diluted with an inert gas such as nitrogen gas. Among these gases, air is particularly preferred.

In carrying out the process of the invention, the reaction temperature may range from room temperature to 100° C. and preferably from 35° to 70° C. If the reaction temperature is below the aforesaid lower limit, the reaction rate will be too low for practical purposes. If the reaction temperature is above the aforesaid upper limit, the formation of by-products will be increased to reduce the yield of the desired product.

The reaction pressure may range from atmospheric pressure to 10 kg/cm$^2$ and preferably from atmospheric pressure to 5 kg/cm$^2$. However, atmospheric pressure is advantageously used in typical cases. The partial pressure of oxygen may range from 0.2 to 2 kg/cm$^2$ and preferably 0.2 to 1 kg/cm$^2$, though partial pressure of oxygen lower than 0.2 kg/cm$^2$ may be used. Higher reaction pressures (or higher partial pressures of oxygen) will enhance the reaction rate but will accelerate lowering of the catalytic activity when the catalyst is used repeatedly over a long period of time. Thus, the use of pressure higher than the aforesaid upper limit is undesirable.

The time required for the reaction depends mainly on the amount of catalyst used and the reaction temperature. However, in the case of a batch system, it usually ranges from 0.5 to 5 hours.

The process of the invention can be carried out either in a batch system or in a continuous system. In typical cases, the reactor is of either the agitated tank type or the bubble tower type, and the catalyst bed is of the suspensoid type. However, the catalyst can also be used in the form of a fixed bed.

After completion of the reaction, the reaction mixture is filtered to remove the catalyst therefrom and the filtrate thus obtained is concentrated to obtain an aqueous solution containing the desired pyruvate. This aqueous pyruvate solution can be directly used in the production of amino acids by the action of enzymes. The pyruvate may be converted into free pyruvic acid by any conventional procedure, as by neutralizing the aqueous pyruvate solution with an acid or by treating it with an ion-exchange resin.

The desired pyruvate, e.g. sodium pyruvate, is preferably isolated from the aforesaid aqueous pyruvate solution in the manner described below. In general, pyruvates are poor in thermal stability. When a pyruvate is produced by the oxidation of a lactate, therefore, it is difficult to separate a highly pure solid pyruvate from the reaction mixture simply by evaporating the resulting aqueous pyruvate solution to dryness. This is because the pyruvate may be polymerized or decarboxylated to form an acetate as a by-product.

According to the present invention, this difficulty is overcome by mixing the aqueous pyruvate solution with isopropyl alcohol. Specifically, the desired pyruvate can be isolated in the form of a solid by mixing the aqueous pyruvate solution with isopropyl alcohol to precipitate the pyruvate, collecting the precipitate by filtration, and then washing and drying it.

The agent which is mixed with the aqueous pyruvate solution to precipitate the pyruvate must be isopropyl alcohol. If lower alcohols other than isopropyl alcohol, such as methanol, ethanol, and butanol, are used, it will be impossible to precipitate the pyruvate from the aqueous pyruvate solution. Though the pyruvate may be precipitated partially, the yield of the precipitate will be too low for practical purposes.

The aqueous pyruvate solution obtained by the process of the invention usually contains small amounts of acetate, as a by-product, and unreacted lactate. It has been difficult to separate the pyruvate from the acetate and the lactate and thereby collect the pyruvate alone in an economical manner. According to the present invention, however, the precipitation of the pyruvate with isopropyl alcohol also serves to separate the pyruvate from the acetate and the lactate because these two compounds are relatively soluble in isopropyl alcohol.

If the aqueous pyruvate solution is colored considerably, it is desirable to treat it with a suitable decolorizing agent, such as activated carbon, prior to the precipitation of the pyruvate with isopropyl alcohol. If this treatment is omitted, the resulting precipitate may be colored.

The concentration of the aqueous pyruvate solution with which isopropyl alcohol is mixed should be in the range of from 20 to 70% by weight and preferably from 30 to 50% by weight. The isopropyl alcohol used for this purpose need not be of high purity and may contain an appreciable amount of water. Accordingly, the mixture of isopropyl alcohol and water resulting from the process of the invention may be simply distilled to recover an azeotropic mixture of 88% of isopropyl alcohol and 12% of water for repeated use. Thus, no special extraction and distillation procedures are required.

The amount of isopropyl alcohol used is in the range of from 2 to 10 parts by volume, and preferably from 4 to 6 parts by volume, per part by volume of the aqueous pyruvate solution.

In practice, isopropyl alcohol is agitated and the aqueous pyruvate solution is added thereto. While the agitation is continued, a white precipitate of the pyruvate is formed. The precipitate is allowed to grow by agitating the mixture for a while, and then collected by filtration. The precipitate thus obtained is washed with anhydrous isopropyl alcohol or acetone, and then air-dried at a temperature ranging from room temperature to 60° C. or dried under reduced pressure.

The present invention is further illustrated by the following examples.

EXAMPLE 1

A 1-liter stainless steel cylinder fitted with a baffle plate, a turbine blade agitator, and an air inlet tube was used as a reactor. Into this reactor were charged an aqueous solution containing 11.2 g of sodium lactate in 150 g of water and 2.5 g of a catalyst composed of activated carbon powder having supported thereon 3% by weight of platinum and 5% by weight of lead nitrate. This reaction mixture was kept at a temperature of 45° C., during which air was blown therethrough at a rate of 150 ml/min and the agitator was operated at a speed of 600 r.p.m.

Two hours after commencement of the reaction, analysis by high-speed liquid chromatography revealed that essentially all the sodium lactate had disappeared. Accordingly, the reaction procedure was discontinued and the catalyst was removed from the reaction mixture by filtration. The filtrate thus obtained was a colorless and clear solution. Upon analysis by high-speed liquid chromatography, this solution was found to contain 10 g of sodium pyruvate. The solution was passed through an ion-exchange column to convert the pyruvate into free pyruvic acid, and then concentrated. Thereafter, the pyruvic acid was precipitated as a condensation product with o-phenylenediamine. Its nuclear magnetic resonance spectrum confirmed that the compound thus obtained was pyruvic acid.

EXAMPLE 2

Into a reactor of the bubble tower type were charged 200 g of an aqueous solution containing 10% by weight of sodium lactate and 4 g of a catalyst composed of activated carbon powder having supported thereon 2% by weight of platinum and 3% by weight of lead carbonate. This reaction mixture was kept at a temperature of 65° C. for a period of 1.5 hours, during which air at atmospheric pressure was blown therethrough.

After completion of the reaction, the catalyst was removed from the reaction mixture by filtration. When the solution thus obtained was analyzed by high-speed liquid chromatography, it was found that the degree of conversion of the sodium lactate was 90%, the selectivity to sodium pyruvate was 85%, and the selectivity to sodium acetate was 5%.

The above solution was concentrated under reduced pressure to a final weight of 50 g, and 100 g of isopropyl alcohol was added thereto and stirred. The white precipitate thus formed was collected by filtration and dried at 45° C. under reduced pressure to obtain 13.7 g of a white powder. The nuclear magnetic resonance spectrum recorded with a solution of the powder in heavy water revealed that the powder was composed of a high purity of sodium pyruvate having very low sodium lactate and sodium acetate contents.

EXAMPLE 3

A 1-liter stainless steel cylinder fitted with a baffle plate, a turbine blade agitator, and an air inlet tube was used as a reactor. Into this reactor were charged 240 g of an aqueous solution containing 24.0 g of sodium lactate in distilled water and 5 g of a catalyst composed of activated carbon powder having supported thereon 2% by weight of platinum and 5% by weight of bismuth hydroxide. This reaction mixture was kept at a temperature of 64° C. by heating externally in a water bath, during which air was blown therethrough at a rate of 250 ml/min and the agitator was operated at a speed of 700 r.p.m.

Two and a half hours after commencement of the reaction, analysis by high-speed liquid chromatography revealed that 90% or more of the sodium lactate had disappeared. At this time, the reaction procedure was discontinued and the catalyst was removed from the reaction mixture by filtration. The filtrate thus obtained was a colorless and clear solution. Upon analysis by high-speed liquid chromatography, this solution was found to contain 20 g of sodium pyruvate, 1 g of condensed pyruvic acid, 2 g of unreacted sodium lactate, and 0.2 g of sodium acetate. Then, the solution was concentrated to half of its original volume. Its nuclear magnetic resonance spectrum showed an absorption peak due to the presence of a methyl proton in pyruvic acid and thus confirmed the formation of the pyruvate.

EXAMPLE 4

The procedure of Example 1 was repeated using the same apparatus and reaction conditions, except that the catalyst was composed of alumina powder having supported thereon 2% by weight of palladium and 5% by weight of bismuth hydroxide. Upon analysis by high-speed liquid chromatography, the resulting solution was found to contain 14 g of sodium pyruvate, 6 g of unreacted sodium lactate, and 2 g of condensed pyruvic acid.

EXAMPLE 5

Into a reactor of the same type as used in Example 1 were charged an aqueous solution containing 11.2 g of sodium lactate in 150 g of water and 2.0 g of a catalyst composed of activated carbon powder having supported thereon 0.5% by weight of platinum, 2.0% by weight of palladium, and 3% by weight of lead carbonate. This reaction mixture was kept at a temperature of 60° C., during which air was blown therethrough at a rate of 250 ml/min and the agitator was operated at a speed of 650 r.p.m.

Two hours after commencement of the reaction, it was found that 90% or more of the sodium lactate had disappeared and 9.5 g of sodium pyruvate had been formed.

EXAMPLES 6-9

The procedure of Example 1 was repeated using the same apparatus and reaction conditions, except that the reaction temperature was 60° C. and the catalyst was 1.5 g of commercially available carbon powder containing 2% by weight of platinum and further having the indicated additional components applied thereto. The results are shown in the following table.

| Example No. | Catalyst | Yield of Sodium Pyruvate (g) | Additional Components |
|---|---|---|---|
| 6 | Pt—Pb—Sn on C | 9.5 | 30 mg lead acetate, 10 mg telluric acid |
| 7 | Pt—Bi—Te on C | 9.8 | 30 mg lead nitrate tin oxychloride |
| 8 | Pt—Pb—In on C | 9.0 | 30 mg lead nitrate, 5 mg indium chloride |
| 9 | Pt on C | 0.85 | |

EXAMPLE 10

Into a reactor of the bubble tower type were charged 200 g of an aqueous solution containing 7% by weight of sodium lactate and 3.0 g of a catalyst composed of activated carbon powder having supported thereon 3% by weight of platinum and 3% by weight of lead carbonate. This reaction mixture was kept at a temperature of 65° C., during which air was blown therethrough. Seventy minutes after commencement of the reaction, it was found that the degree of conversion of the sodium lactate was 90% and the selectivity to sodium pyruvate was 89%.

An air inlet means consisting of a sintered metal plate was provided at the bottom of the reactor. After completion of the reaction, the reaction mixture was removed through the sintered metal plate, so that the catalyst was retained in the reactor without any loss.

Then, 200 g of an aqueous solution containing 7% by weight of sodium lactate was charged again into the reactor and allowed to react under the same conditions as described above. Thus, the reaction was repeated 24 times. Two hours after commencement of the 24th reaction cycle it was found that the degree conversion of the sodium lactate was 90% and the selectivity to sodium pyruvate was 84%.

What is claimed is:

1. A process for producing a salt of pyruvic acid by the oxidation of a salt of lactic acid which comprises oxidizing at a temperature of from room temperature to 100° C. a 2–30 weight 0/0 concentration of said salt of lactic acid with an oxygen-containing gas in a water-containing solvent in the presence of a catalyst comprising (a) at least one component selected from the group consisting of platinum and palladium and (b) a component selected from the group consisting of lead, tin, tellurium, indium, bismuth, and oxides, hydroxides, nitrates, sulfates, halides, carbonates, acetates and propionates of these elements, whereby forming the salt of pyruvic acid.

2. A process as claimed in claim 1 wherein the components (a) and (b) are supported on a carrier selected from the group consisting of activated carbon and alumina.

3. A process as claimed in claim 1 wherein the catalyst is composed of activated carbon powder having supported thereon from 0.5 to 10% by weight, based on the weight of the powder, of the component (a) and from 0.5 to 10% by weight, based on the weight of the powder, of the component (b).

4. A process as claimed in claim 3 wherein the catalyst is composed of activated carbon powder having supported thereon from 1 to 5% by weight of platinum and from 1 to 5% by weight of bismuth or a bismuth compound selected from bismuth nitrate, bismuth carbonate, bismuth hydroxide and bismuth oxide.

5. A process as claimed in claim 3 wherein the catalyst is composed of activated carbon powder having supported thereon from 1 to 5% by weight of platinum and from 1 to 5% by weight of lead or a lead compound selected from lead nitrate, lead carbonate, lead acetate, lead hydroxide and lead oxide.

6. A process as claimed in claim 3 wherein the catalyst comprises activated carbon powder having supported thereon from 1 to 5% by weight of palladium and from 1 to 5% by weight of lead or a lead compound selected from lead nitrate, lead carbonate, lead acetate, lead hydroxide and lead oxide.

7. A process as claimed in claim 3 wherein the catalyst comprises activated carbon powder having supported thereon from 1 to 5% by weight of palladium and from 1 to 5% by weight of bismuth or a bismuth compound selected from bismuth nitrate, bismuth carbonate, bismuth hydroxide and bismuth oxide.

8. A process as claimed in claim 3 wherein the catalyst comprises activated carbon powder having supported thereon from 1 to 5% by weight of the component (a) and from 1 to 5% by weight of the component (b).

9. A process as claimed in claim 1 wherein the water-containing solvent is water.

10. A process as claimed in claim 1 wherein the concentration of the salt of lactic acid in the water-containing solvent is in the range of from 5 to 20% by weight.

11. A process as claimed in claim 1 wherein the salt of lactic acid is sodium lactate.

12. A process as claimed in claim 1 wherein the oxidation reaction is carried out at a temperature ranging from 35° C. to 70° C.

13. A process according to claim 1 wherein said component (b) of said catalyst is lead acetate admixed with telluric acid, lead nitrate admixed with indium chloride, or lead nitrate admixed with tin oxychloride.

14. A process as claimed in claim 1 wherein the oxidation reaction is carried out under a total pressure of from atmospheric to 10 Kg/cm$^2$ under a partial pressure of oxygen of 0.2 to 2 Kg/cm$^2$.

15. A process as claimed in claim 14 wherein the oxidation reaction is carried out under a total pressure ranging from atmospheric pressure to 5 kg/cm$^2$ and under a partial pressure of oxygen ranging from 0.2 to 1 kg/cm$^2$.

16. A process as claimed in claim 1 wherein the oxygen-containing gas is air.

17. A process for producing a solid salt of pyruvic acid by the oxidation of a salt of lactic acid which comprises oxidizing at from room temperature to 100° C. a 2–30 weight 0/0 concentration of the salt of lactic acid with an oxygen-containing gas in a water-containing solvent in the presence of a catalyst comprising (a) at least one component selected from the group consisting of platinum and palladium and (b) a component selected from the group consisting of lead, tin, tellurium, indium, bismuth, and oxides, hydroxides, nitrate, sulfates, halides, carbonates, acetates and propionates of these elements to form the salt of pyruvic acid; removing the catalyst from the reaction mixture; and then precipitating the resulting pyruvate from the reaction mixture by mixing therewith isopropyl alcohol in an amount equal to from 2 to 10 times the volume of the reaction mixture.

18. A process as claimed in claim 17 wherein, prior to the addition of isopropyl alcohol, the catalyst-free reaction mixture is concentrated until the concentration of the pyruvate comes within the range of from 20 to 70% by weight.

19. A process as claimed in claim 17 wherein the catalyst is composed of activated carbon or alumina having supported thereon the components (a) and (b).

20. A process as claimed in claim 17 wherein the oxidation reaction is carried out at a temperature ranging from 35° to 70° C. and under a pressure ranging from atmospheric pressure to 5 kg/cm$^2$.

21. A process as claimed in claim 17 wherein the amount of isopropyl alcohol mixed is equal to from 4 to 6 times the volume of the reaction mixture.

22. A process as claimed in claim 18 wherein the catalyst-free reaction mixture is concentrated until the concentration of the pyruvate comes within the range of from 30 to 50% by weight.

* * * * *